United States Patent [19]

Doutheau et al.

[11] Patent Number: 4,767,872
[45] Date of Patent: Aug. 30, 1988

[54] EPOXIDE DERIVATIVES

[75] Inventors: Alain Doutheau, Lyons; Jacques Goré, Caluire; Gerard A. Quash, Francheville; Bernard Didier, Lyons, all of France

[73] Assignees: Centre National de la Recherche Scientifique (CNRS); Institut National de la Sante et de la Recherche Medicale (INSERM), both of Paris, France

[21] Appl. No.: 824,871

[22] Filed: Jan. 31, 1986

[30] Foreign Application Priority Data

Feb. 1, 1985 [FR] France ................. 85 01426

[51] Int. Cl.$^4$ ............................. C07D 303/36
[52] U.S. Cl. ........................... 549/551; 514/908
[58] Field of Search ........................ 549/551

[56] References Cited

FOREIGN PATENT DOCUMENTS 0130829 1/1985 European Pat. Off. .

Primary Examiner—Norma S. Milestone
Attorney, Agent, or Firm—Cushman, Darby & Cushman

[57] ABSTRACT

A compound of the formula

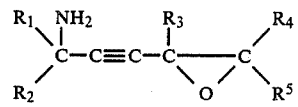

wherein $R_1$ and $R_2$ each independently represent a hydrocarbon group which can be substituted and/or carry a heteroatom, or $R_1$ and $R_2$ together represent a hydrocarbon, optionally substituted, forming with the carbon atom to which they are attached, a ring capable of carrying a heteroatom, $R_3$ represents hydrogen, lower alkyl or aryl, and $R_4$ and $R_5$ each independently represent hydrogen or a hydrocarbon group, as well as the acid addition salts thereof. A method of preparing the compounds and the use thereof as an anti-tumor medicine are disclosed.

1 Claim, No Drawings

EPOXIDE DERIVATIVES

The present invention relates to a new epoxide derivative possessing enzyme inhibiting activity, to its preparation and to its use, principally, as antitumor medicine.

It is known that reductase aldehyde (RALD) is one of the enzymes that intervenes in the process of producing malonic aldehyde starting with polyamines by transforming this aldehyde into 1,3-propanediol and by thus preventing its accumulation in the cellular medium.

New epoxide derivatives have now been discovered which derivatives are RALD inhibitors and are capable of inhibiting the growth of transformed cells.

The present invention relates to compounds of the following general formula I:

$$\begin{array}{c} R_1 \quad NH_2 \quad R_3 \quad R_4 \\ \diagdown | \quad | \quad / \\ C-C\equiv C-C-\!\!\!\!-C \\ / \quad \diagdown / \diagdown \\ R_2 \quad O \quad R_5 \end{array} \quad (I)$$

wherein $R_1$ and $R_2$, each independently, represent a hydrocarbon group capable of being substituted and/or carrrying heteroatoms, or $R_1$ and $R_2$ together represent a hydrocarbon group, optionally substituted, forming, with the carbon atom to which they are attached, a ring capable of carrying heteroatoms, $R_3$ represents hydrogen, a lower alkyl group or aryl, and $R_4$ and $R_5$ each independently represent hydrogen or a hydrocarbon group.

Representative compounds of formula I include:

those for which $R_1$ and $R_2$ each independently represent alkyl having 1–5 carbon atoms; or $R_1$ and $R_2$ together represent pentamethylene;

those for which $R_3$ represents alkyl having 1–5 carbon atoms or phenyl;

those for which $R_4$ and $R_5$ each represent hydrogen;

or even those for which one of the $R_4$ and $R_5$ substituents represent hydrogen and the other represents alkyl having 1–5 carbon atoms.

The present invention also concerns the addition salts of the compounds of formula I, which salts principally are those formed with acids compatible with a therapeutic use.

The present invention also relates to a process for preparing the compounds of formula I.

This process comprises reacting a compound of formula II:

$$\begin{array}{c} R_1 \quad NH_2 \\ \diagdown | \\ C-C\equiv C-Z_1 \\ / \\ R_2 \end{array} \quad (II)$$

wherein $Z_1$ represents either hydrogen or one equivalent of a metal or of a group linked to the carbon atom to which it is attached by a carbon-metal bond, with an α-halogenated carbonyl derivative of formula III:

$$\begin{array}{c} R_3 \quad X \quad R_4 \\ | \quad | \; / \\ O=C-C \\ \diagdown \\ R_5 \end{array} \quad (III)$$

wherein $R_3$, $R_4$ and $R_5$ have the meanings given above and X represents halogen, so as to obtain a halohydrin of formula IV:

$$\begin{array}{c} R_1 \quad NH_2 \quad R_3 \quad R_4 \\ \diagdown | \quad | \quad / \\ C-C\equiv C-C-C \\ / \quad | \; | \; \diagdown \\ R_2 \quad OH \; X \quad R_5 \end{array} \quad (IV)$$

wherein $R_1$, $R_2$, $R_3$, $R_4$, $R_5$ and X have the meanings given above. Thereafter, the said compound of formula IV is submitted to the action of a base, so as to obtain a compound of formula I. If necessary, the amine group of the resulting compound can be salified.

The initial reactants of formula II are known or can be prepared according to known methods, for example, according to the method described by G. F. Hennion and E. G. Teach, J. Org. Chem., 1972, 17, 1653.

The derivatives of formula III can be prepared in accordance with general methods of preparing α-halo carbonyl derivatives.

The process of the present invention can also exhibit the following characteristics, singly or in combination:

The organometallic derivatives of formula II are principally those for which $Z_1$ represents an alkali metal or a —MgHal group, Hal being a halogen; for example before reaction with the carbonyl derivative of formula III, a compound of formula II (with $Z_1$=H) is initially transformed into a corresponding metallic derivative (notably organolithium or organomagnesium) according to conventional procedures; in particular the compound of formula II ($Z_1$=H) is reacted with a lithium alkyl to form the corresponding lithium derivative of formula II ($Z_1$=Li); or indeed and, in accordance with conventional procedures, a corresponding organomagnesium derivative is prepared.

To transform the halohydrin of formula IV into the compound of formula I, known epoxide synthesis conditions starting with halohydrins are employed, that is the halohydrin is treated in the presence of a base such as an alkaline alcoholate, for example, alkaline tert.butylate.

The compounds of formula I can be transformed into any corresponding addition salt by the action of an acid, for example, a halohydric acid.

The invention also relates to an intermediate product obtained during the operation of the process described above. These intermediate products are those of formula IV wherein $R_1$, $R_2$, $R_3$, $R_4$, $R_5$ and X are defined above.

The compounds of formula I, as well as their acid addition salts, exhibit satisfactory stability characteristics. They possess interesting pharmacological properties, principally their ability to inhibit the enzymatic activity of aldehyde reductase.

It has also been discovered that the compounds of the present invention are capable of selectively acting on transformed cells by blocking cellular division, and of selectively inhibiting the growth of the said transformed cells, whereas the inhibition of the growth of normal cells is zero or very small.

These properties, together with a reduced toxicity, permit the use of the compounds of formula I, or their acid addition salts, principally in the treatment of cancer, as an anti-tumor agent.

In particular, the compounds of formula I are useful in the treatment of forms of cancer, for example, certain leukemias, characterized by an increase in reductase aldehyde activity in tumoral cells relative to normal cells; see principally R. Felsted et Coll., "Human liver Daunorubicin-Reductases", in Progress in Clinical and Biological Research, Vol. 114, Ed. Alan R. Liss Incorp., 1982, pp 291-305.

The present invention also concerns, in particular, pharmaceutical compositions containing as the active ingredient at least one compound of formula I or a corresponding acid addition salt.

These pharmaceutical compositions also include an excipient so as to permit the administration of the medicine, orally, intratumorally, intramuscularly or intravenously, or even in the form of an implant. the posology varies with the illness being treated, the mode of administration and the state of illness. Generally, a daily dosage of the compound of formula I varies from 10 to 500 mg/kg of body weight.

The present invention also relates to a pharmaceutical composition which comprises a combination of a compound of formula I with another anti-tumor agent. The invention concerns, in particular, the combination of a compound of formula I with a compound of the formula:

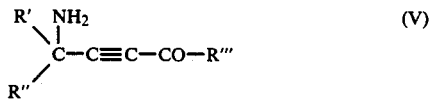

(V)

wherein R' and R" each independently represent a hydrocarbon group, optionally substituted, and/or carrying heteroatoms, or indeed R' and R" together represent a hydrocarbon group, optionally substituted, forming, with the carbon atom to which they are attached, a ring capable of carrying heteroatoms, and R''' represents hydrogen, lower alkyl or —NH$_2$; as well as with functional derivatives of the carbonyl group, and the acid addition salts of these compounds of formula V. Representative compounds of formula V include principally:

those for which R' and R" each represent an alkyl group having 1-5 carbon atoms;

those for which R' and R" represent an alkylene group having 4 to 5 carbon atoms in the chain; and those for which R''' represents hydrogen or an alkyl group having 1-5 carbon atoms.

Representative functional derivatives of the carbonyl group of the compounds of formula V, include, principally, the dialkyl ketals.

The compounds of formula V, as well as their derivatives and acid addition salts, described in French Patent No. 83.12863 filed Aug. 4, 1983 and entitled, "New acetylenic derivatives possessing enzyme inhibiting activity, their preparation and use as a medicine".

These compounds of formula V are anti-tumor agents which exhibit pharmacologic properties different from those of the compounds of the present invention. In particular, the compounds of formula V are inhibitors of dehydrogenase aldehyde.

In the treatment of tumors, the compounds of formula I can also advantageously be combined with other known anti-tumor agents such as daunorubicin and adriamycin.

The present invention also relates to the use of the compounds of formula I, as well as their acid addition salts, in the industrial preparation of anti-tumor medicines.

The present invention further concerns the use of the compounds of formula I in the detection of a cancerous or pre-cancerous state of cells from a biopsy.

In effect, it has been observed that not only is reductase aldehyde activity increased in malignant cells, but also that this activity is increased at an early stage in benign transformed cells which is characterized as being a pre-cancerous state. An inhibition test of cellular growth, using a compound of formula I, permits then an early diagnosis.

Moreover, the diagnosis can be specified by conjointly employing an inhibition test of dehydrogenase aldehyde activity using a compound of formula V. In effect, dehydrogenase aldehyde activity is modified in malignant cells, but not in benign transformed cells.

The test permitting the characterization of these modifications of cellular activity can be, for example, a test of cellular growth in the presence of a compound of formula I, and a test of cellular growth in the presence of a compound of formula V. If the compounds of formulas I and V both inhibit cellular growth, this characterizes a cancerous state, whereas inhibition by the compounds of formula I alone characterizes a pre-cancerous state.

The following non-limiting examples illustrate the present invention.

EXAMPLE 1

Preparation of an epoxide of formula I wherein $R_1=R_2=R_3=CH_3$ and $R_4=R_5=$ hydrogen (a) To a solution of 2.08 g (0.025 mole) of propargyl amine in 100 ml of anydrous tetrahydrofuran, cooled to $-60°$ C., there are added, under a nitrogen atmosphere, 18.5 ml (0.03 mole) of a 1.65 M solution of n-butyl lithium in hexane.

The temperature of the reaction mixture is permitted to rise, over a 30-minute period, to $-5°$ C. at which point the reaction mixture is again cooled to $-60°$ C., before adding a solution of 2.20 g (0.024 mole) of 1-chloro-2-propanone in 5 ml of anhydrous THF. The temperature is then permitted to rise to 20° C. over a 3-hour period.

The reaction mixture is diluted with ethyl ether and then hydrolyzed with 10 ml of a saturated NH$_4$Cl solution. After a conventional treatment, 3.72 g of 6-chloro-5-hydroxy-2,5-dimethyl-3-hexyne-2-amine (yield-85%) are recovered. Melting point - 38-40° C. (ether).

NMR and IR spectra confirm the indicated structure.

(b) to a solution of 1.76 g (0.01 mole) of the chlorhydrin, obtained in step (a), in 50 ml of anhydrous ethyl ether and cooled to $-20°$ C., there are added, with vigorous stirring, 1.41 g (0.013 mole) of potassium tert-.butylate.

The temperature of the reaction mixture is permitted to rise to 20° C. over a 30 minute period at which point it is washed twice with 10 ml of a saturated NaCl solution. After a conventional treatment, 1.09 g of 5,6-epoxy-2,5-dimethyl-3-hexyne-2-amine are recovered (yield - 78%.)

IR: 3340, 3280, 3040, 2220, 1590, 1370, 1270 nm

NMR: dimethyl group, 1.25s, (6H); methyl group, 1.40s, (3H); NH$_2$ group, 1.45s, (2H); Methylene group, 2.50 d(J+6Hz), (1H); 2.75 d; M$^+$mass=139 (1), 138(2), 124(100) 108(15), 94(31), 82(14), 67(17), 58(9), 42(34).

EXAMPLE 2

Study of pharmacologic properties (a) In vitro test

Cellular homogenates of NRK B77 cells which contain about 500 micrograms of the enzyme are prepared and incubated with the compound of Example 1 at doses of 0.2 mM, 0.8 mM and 1 mM. The incubation lasts for 15, 30 or 60 minutes.

After incubation, an aliquot is added to the substrate which is 2 mM malonic dialdehyde dissolved in a phosphate buffer of pH 6 containing 0.35 mM of NADPH (co-factor of the enzyme).

The optical density is measured every minute, for 5 minutes, at 340 nm.

The transformation of NADPH into NADD causes a linear reduction of the optical density. The inhibiting effect is evaluated by the difference between the variation of the optical density in the controls (without inhibitor) and the variation of the optical density with the inhibitor.

At a dosage of 1 mM, the compound of Example 1 causes total inhibition of the RALD activity at the end of 30 minutes. With 0.2 mM, the remaining activity is lower than 25% at the end of 60 minutes. At a dosage of 0.8 mM, the remaining RALD activity at the end of 30 minutes is about 10%.

(b) Growth inhibition of transformed cells.

The tests are carried out in the following manner:

A culture medium, constituted by the Eagle minimum medium to which has been added 10% of calf serum, is seed with $2 \times 10^5$ cells being studied.

At the end of 4 hours after seeding, the compound of formula I is added at the dosages indicated in the following table. After 4 days of culture, the inhibition relative to non-treated control cultures is measured.

The results are indicated in Table I below.

(c) Toxicity

The study of the toxicity has been carried out on mice. The product of Example 1 is administered intraperitoneally at a dosage of 3 g/kg body weight daily for 8 days. No apparent toxicity has been detected.

The DL50 is then greater than 3 g/kg.

TABLE 1

Effect of the Product of Example 1 on the Cellular Growth Expressed as a Percentage of Inhibition

|  | $5 \times 10^{-5}$ M | $1 \times 10^{-4}$ M | $2 \times 10^{-4}$ M | $4 \times 10^{-4}$ M | $6 \times 10^{-4}$ M |
|---|---|---|---|---|---|
| Normal diploid cells MRC5 | 0 | 0 | 0 | 0 | 0 |
| Established lines NRK Transformed cells | — | — | 30 | 60 | Dead |
| HeLa | 0 | 0 | 20 | 80 | 90 |
| HEp2 | 0 | 0 | 20 | 80 | Dead |
| 293 | 20 | 50 | 90 | Dead | Dead |
| NRK B77 | 0 | 0 | 0 | 50 | 60 |

NRK: kidney cells of normal rats
NRK B77: kidney cells of rat transformed by the virus of Rous Sarcoma (Strain B77)
Hela: human uterine carcinoma
MRC5: Normal fibroblasts of human embryonic lung
HEp2: human larynx carcinoma
293 human embryonic kidney transformed by the DNA of type 5 adenovirus.

EXAMPLES 3 to 5

In a manner analogous to that described in Example 1, starting with corresponding compounds of formulas II and III, the following compounds of formula I have been prepared.

| Example | $R_1$ | $R_2$ | $R_3$ | $R_4$ | $R_5$ |
|---|---|---|---|---|---|
| 3 | $CH_3$ | $CH_3$ | $CH_3$ | $CH_3$ | H |
| 4 | $CH_3$ | $CH_3$ | $C_6H_5$ | H | H |
| 5 | $CH_3$ | $CH_3$ | H | H | H |

These compounds possess, principally, an inhibiting activity of the growth of transformed cells.

EXAMPLES 6 and 7

In an analogous manner, starting with corresponding compounds of formulas II and III, the following compounds have been prepared.

| EXAMPLE | $R_1$ | $R_2$ | $R_3$ | $R_4$ | $R_5$ |
|---|---|---|---|---|---|
| 6 |  | —$C_5H_{10}$— | $CH_3$ | H | H |
| 7 | $CH_3$ | $C_2H_5$ | $CH_3$ | H | H |

EXAMPLE 8

Detection of transformed cells in a biopsy

As indicated above, the compounds of formula I can be used to detect a cancerous or pre-cancerous state of cells from a biopsy.

The present invention thus also relates to a process for the detection of the cancerous or pre-cancerous state of cells from a biopsy, characterized by the fact that culture cells from the biopsy are placed in an appropriate culture medium, respectively in the presence of and in the absence of a compound of formula I, the compound of formula I being introduced, when it is present, at a concentration at which it inhibits the growth of known transformed cells. This concentration ranges, for example, from $10^{-5}$M to $10^{-2}$M for a culture containing at least $10^5$ cells being studied at the moment of addition of the compound of formula I. The growth of the cultivated cells in the presence of the compound of formula I is then compared to the growth of the cells in the absence of the compound of formula I, it being understood that a significant inhibition, for example, at least 50%, of the growth of the cells, relative to cells in non-treated cultures, means that the biopsy contained transformed cells (benign or malignant).

The preceding detection test can be completed by a complementary test, which is also an object of the present invention, this complementary test establishing whether or not the transformed cells are benign or malignant cells.

The present invention consequently also relates to a process for detecting malignant cells optionally present in a biopsy, characterized by the fact that cultures of cells are produced from the biopsy in an appropriate culture medium, respectively in the presence of and in the absence of a compound of formula V which is introduced, when it is present, at a concentration at which the compound of formula V inhibits the growth of known malignant cells. The growth of the cells in the presence of the compound of formula V is then compared to the growth of the cells in the absence of the compound of formula V, it being understood that a significant inhibition, for example, at least 50% of the growth of the cells, relative to the cells of the non-treated culture, means that the biopsy contained malignant transformed cells. In the situation where the starting cells have already been submitted to the test described above concerning the use of a compound of formula I, not only can it be determined that the biopsy contains transformed cells, but also a determination can be made whether or not the transformed cells are benign cells or malignant cells.

The compound of formula V is used, for example, at a concentration of $10^{-5}$M to $10^{-2}$M for a culture containing at least $10^5$ cells at the moment of the addition of the compound of formula V.

In practice the tests are carried out with increasing concentrations of the product of formula V.

The test for the detection of transformed cells with a compound of formula I can be effected, for example, according to the process described above in Example 2 (b).

The detection test permitting to distinguish between benign transformed cells and malignant transformed cells, with the aid of a compound of formula V can be effected, for example in the following manner.

Petri dishes having a diameter of 10 cm are seeded with $10^6$ cells to be studied. At the end of 4 hours after seeding, the compound of formula V (with $R'=R''=CH_3$, $R'''=H$) is added in the form of an aqueous solution containing 0.14 M NaCl, the solution having a volume of 100 microliters. The effect of the compound of formula V is studied at various concentrations. The following results set forth in Table II have been obtained CEC signifies a culture of normal cells of chicken embryo. The cells can be cultivated only with a limited number of passages (3 to 5).

MRC5 is a culture of normal cells (fibroblasts of embryonic human lung). These known cells, which can be cultivated only with a limited number of passages (28 to 30), have been furnished by Institut Merieux, Lyon, France.

NRK (ATCC CRL 1571): a culture of cells of rat kidney, cultivatable indefinitely, but not giving rise to tumors when they are injected; they are then benign transformed cells.

NRK B77: These are transformed cells of rat kidney, cultivatable indefinitely, and giving rise to tumors when they are injected: these are then malignant cells. The NRK B77 cells used have been furnished bby Dr. Thomas Graf, Heidelberg.

HeLa: This is a well known malignant human cell line (ATCC CCL2).

What is claimed is

1. A compound of the formula

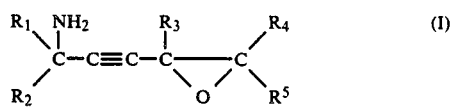

wherein $R_1$ and $R_2$ each independently represent alkyl having 1-5 carbon atoms, or $R_1$ and $R_2$ taken together represent pentamethylene, $R_3$ represents hydrogen, alkyl having 1-5 carbon atoms or phenyl;

$R_4$ and $R_5$ represent hydrogen, or one of said $R_4$ and $R_5$ represents hydrogen and the other represents alkyl having 1-5 carbon atoms, and the acid addition salts thereof.

* * * * *

TABLE II

| | Concentration employed | | | | |
|---|---|---|---|---|---|
| | $0.5 \times 10^{-5}$ M | $1 \times 10^{-4}$ M | $2 \times 10^{-4}$ M | $4 \times 10^{-4}$ M | $6 \times 10^{-4}$ M |
| Normal cells | | | | | |
| CEC | 0 | 0 | 0 | 10 | 12 |
| MRC5 | 0 | 0 | 0 | 0 | 18 |
| Established cell lines (benign transformed cells) | | | | | |
| NRK | 0 | 0 | 0 | 0 | 0 |
| Malignant cells | | | | | |
| NRK B77 | 0 | 16 | 31 | 57 | 79 |
| HeLa | 0 | 18 | 36 | 78 | 91 |